United States Patent [19]

Emerson

[11] Patent Number: 4,611,495

[45] Date of Patent: Sep. 16, 1986

[54] ULTRASONIC TESTING

[75] Inventor: Peter J. Emerson, Alcester, England

[73] Assignee: BCIRA, Birmingham, England

[21] Appl. No.: 647,435

[22] Filed: Sep. 5, 1984

[30] Foreign Application Priority Data

Sep. 8, 1983 [GB] United Kingdom ............... 8324109

[51] Int. Cl.$^4$ ............................................. G01N 29/04
[52] U.S. Cl. ......................................... 73/634; 73/644
[58] Field of Search .................. 73/634, 644, 655, 661

[56] References Cited

U.S. PATENT DOCUMENTS 3,678,736  7/1972  May .......................................... 73/634
4,370,889  2/1983  Ruthrof et al. ........................ 73/619

FOREIGN PATENT DOCUMENTS 2111682  7/1983  United Kingdom .

Primary Examiner—Anthony V. Ciarlante

Attorney, Agent, or Firm—Scrivener Clarke Scrivener and Johnson

[57] ABSTRACT

In the ultrasonic testing of a casting for defects an ultrasonic probe is mounted in a tank of water and scans across a surface of the casting which faces downwards just below the surface of the water. A pantograph linkage interconnects the probe with a pointer that is movable by an operator over a facsimile of the surface scanned by the probe. The interconnection is such that each position of the probe is represented by a corresponding position of the pointer and as the pointer is moved over the facsimile of the surface the probe scans the surface of the casting. The water ensures that there is good acoustic coupling between the probe and casting and the pantograph linkage reduces the skill and concentration required by the operator. Conveniently, only anomalous signals arising from defects are passed on from the probe to the operator.

13 Claims, 3 Drawing Figures

ULTRASONIC TESTING

This invention relates to ultrasonic testing of solid bodies for defects, in particular of metal castings, although it could well find use in the testing of other materials.

The purpose of testing castings is to detect internal unsoundness, which may be in the form of pinholes, blowholes, cracks or various forms of shrinkage porosity.

Cylinder heads for multi-cylinder liquid cooled internal combustion engines are amongst the most difficult bodies to cast free from defects, containing, as they do, a number of curved passages, some of which are visible on the surface, and some of which are not. Conventional ultrasonic inspection may be applied over a flat surface of the casting by a highly skilled operator who is familiar with the internal shape of the casting and with the likely locations where unsoundness may occur. He has to make allowances for varying thicknesses of the casting and avoid the positions where cored passages may approach or vary in distance from the surface. An ultrasonic probe or a series of probes may be used, and they have to be carefully coupled to the surface of the casting, generally by the use of grease or some liquid. As the probe moves around, so must the coupling be maintained.

In such manual testing the signals from the probes appear as traces on the screen of a cathode ray tube, indicating the position of the echo from the back wall of the casting, as well as any signals from defects. The operator has to observe the screen as well as the position of the probe; he has to interpret the signal in relation to the known geometry of the casting and he has to maintain good contact between the probe and the casting. All this is time-consuming, tedious, and requires both skill and concentration.

The aim of the present invention is to allow the automatic or at least semi-automatic repetitive ultrasonic inspection of castings or other bodies at a speed which is at least comparable with that of a skilled manual operator but with the tediousness and concentration reduced and the standard of skill that is required likewise reduced.

According to the invention this is achieved by a linkage which interconnects an ultrasonic probe in contact with the casting or other body with a pointer that is moved by the operator over a drawing or a template that represents the area of the surface of the casting to be tested.

For example a conventional pantograph linkage may be used; as the operator scans the drawing or template with the pointer, the probe scans the corresponding points on the casting itself. Instead of a pantograph linkage, we could use a system of rods sliding in two orthogonal directions, although the pantograph has the advantage of being able to magnify or reduce the movement, so that the drawing or template could be to a scale other than 1:1. In a further development the linkage could be non-mechanical, for example a form of X-Y plotter controlling a servo linkage that actuates the probe, so that the positions of the casting and of the table bearing the drawing or template could be wholly independent of one another, the only connection being through electrical cables carrying coded digital signals. Indeed the drawing itself need not be on paper but could be an image displayed on the screen of a cathode ray tube, with a pointer in the form of a light pen.

According to a further important feature of the invention the surface of the casting or other body to be scanned faces downwards and lies at or just below the surface of a body of liquid, preferably water, in which the probe is mounted. In this way the problem of effective coupling is solved at a stroke. The probe is mechanically urged upwards into contact with the surface of the body, for example by spring-loaded links, and preferably, according to yet another feature of the invention, there are means, such as electrical strain gauges on the links, for monitoring continuously the contact force.

The invention also includes a further possible step to simplify the operation, namely an arrangement which, by gating the signal from the probe in conjunction with information on the instantaneous position of the probe, eliminates signals from known sources such as the back wall of the casting, or the wall of a cored cavity in a known position, and passes on only anomalous signals, i.e. those arising from defects. Furthermore, the occurrence of such anomalous signals is displayed not, or at least not only, on the screen of a cathode ray tube, but either by a light on the pointer itself or in audible form, for example in earphones, or both. Thus the operator no longer has to be continually looking up at a screen but can concentrate his attention wholly on the pointer. In a further development it would be possible for the signal to cause a mark to be made on the drawing or template, and/or on the body itself at that point on the surface below which there is a defect.

Generally speaking, the surface to be inspected must be flat. The operator could can the whole surface, but in some cases the inspection can be confined to a limited area in which defects are known to be liable to occur. In such a case we may use a sheet metal template, cut out to the shape of the area to be scanned, and mount a proximity sensor on the pointer, acting to isolate the signal circuit except when the pointer is in the area of the template.

An example of a system in accordance with the invention is illustrated diagrammatically in the accompanying drawings, in which.

Figure 1:
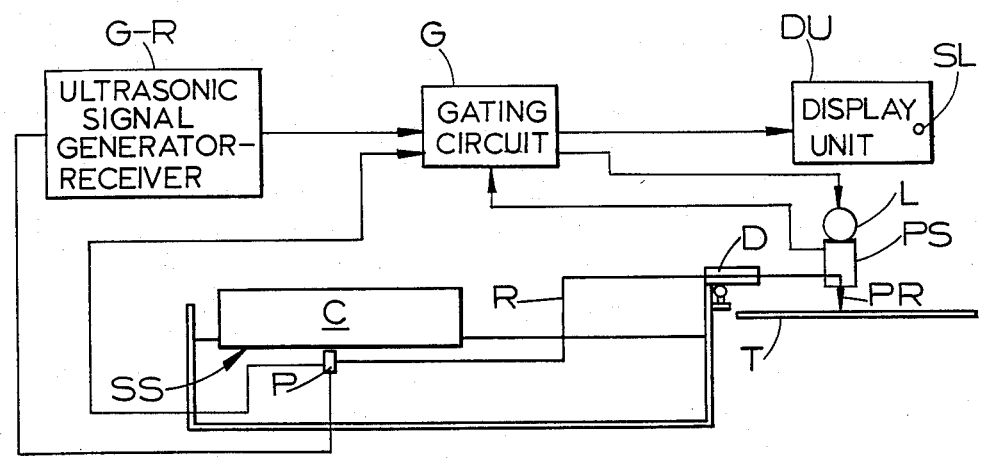
FIG. 1 is a side elevation of the equipment.
Figure 2:
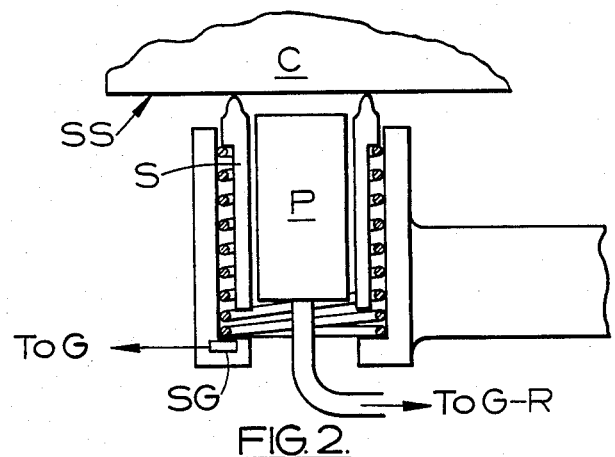
FIG. 2 is a close-up view of the mounting for the probe.
Figure 3:
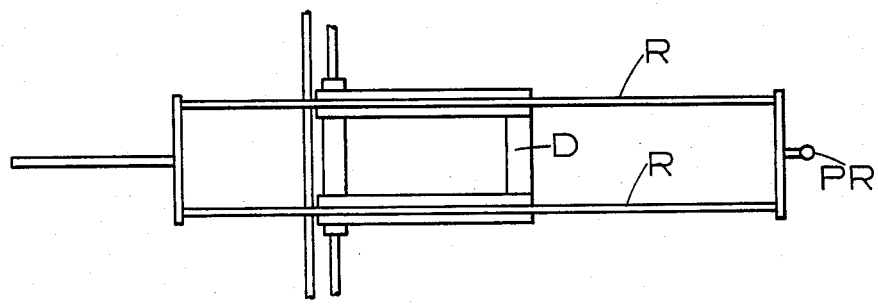
FIG. 3 is a plan view of the interconnecting linkage.

In the example shown the linkage between the probe P and the pointer PR is mechanical and is of the sliding rod kind, with a pair of parallel rods R free to slide horizontally in the direction of their lengths in a carriage D which is free to slide in a horizontal perpendicular direction. The probe P is connected to an ultrasonic signal generator-receiver G-R and is mounted in a sleeve S which spaces it a known constant small distance away from the casting C, and is itself spring-urged into contact with the casting. Strain gauges SG measure the force with which the probe is urged towards the surface and illuminate a signal lamp SL on a display unit DU in the view of the operator when the force is within the correct range. The occurrence of anomalous signals may be displayed visually on the display unit DU and/or by audible signals produced by the display unit and/or by a light L on the pointer PR itself. The path for anomalous signals from the ultrasonic signal generator-receiver to the display unit such as those arising from defects is disabled by a gating circuit G when the force measurement shows that the probe holder is not in contact with the casting.

The casting C is located accurately in a jig with the surface SS that is to be inspected facing downwards and just immersed in a tank of water (which preferably contains a corrosion-inhibiting agent). In this way, good acoustic coupling with the probe is achieved, yet without the water reaching the cored cavities in the casting, which would introduce the need for a subsequent drying-out step.

The surface over which the pointer PR is moved could be a drawing, but is preferably a template T in the form of a metal facsimile of the area to be scanned and, as mentioned, is used in conjunction with a proximity sensor PS on the pointer which is connected to the gating circuit to disable the signal path when the probe is outside the area to be inspected.

The probe P is a double probe in order to obtain maximum sensitivity to defects near the surface SS, as well as those further into the section. The sensitivity to near surface defects is controlled by adjusting the gap between the probe face and the casting by means of the spacer.

Although it would be possible for the casting to be automatically marked at exactly those points on the surface below which defects are observed, in practice we prefer to mark only the point at the edge of the casting, or of the inspected area, on the line of which the defect lies. Equally, we prefer not to mark the facsimile, since this would require a new template or drawing to be used to each casting.

It will be understood that, when the test is complete, the pointer PR is lifted away from the paper or template, and this automatically moves the probe P away from the casting, allowing a fresh casting to be placed in the jig.

As in known ultrasonic test equipment, the position of the electronic gate, the gain and the threshold level of the electronic signal-handling circuits between the probe and the light on the pointer are adjustable, to allow response to different forms and depths of defect. This adjustment may be made automatic, for example by using facsimiles of different colours for different castings and having a colour-sensitive sensor on the pointer which automatically sets the circuits to the required values.

It is important that air bubbles trapped in the rough surface of the casting as it is placed in position should not come between the surface and the probe; this can be avoided by passing a continuous non-turbulent flow of water across the surface of the casting. If the probe carrier is made of slotted construction, this flow of water will also help to carry clear any sand or other debris that might fall from the surface of the casting onto the probe.

I claim:

1. Apparatus for the ultrasonic testing of a casting or other body for defects comprising an ultrasonic probe which is arranged in use to scan a surface of the casting or other body, a drawing or a template that represents the area of the surface of the casting or other body to be scanned by said probe, a pointer that is movable by an operator over said drawing or template, a linkage which interconnects said probe with said pointer in such a manner that as said pointer is moved over said drawing or template said probe scans the surface of the casting and each position of said probe is represented by a corresponding position of said pointer, ultrasonic signal generating-receiving means connected to said probe, gating means connected to said ultrasonic signal generating-receiving means, display means connected to said gating means and responsive to signals from said ultrasonic signal generating-receiving means for indicating when a defect is detected in the casting or other body by said probe, and proximity sensing means associated with said pointer for sensing when said pointer is in the area of said drawing or template and connected to said gating means, whereby said gating means prevents the passage of signals from said ultrasonic signal generating-receiving means to said display means except when said pointer is in the area of said drawing or template.

2. Apparatus according to claim 1 wherein said linkage comprises a system of rods sliding in two orthogonal directions.

3. Apparatus according to claim 1 comprising a body of liquid in which the probe is mounted and holding means for holding the casting or other body in such a manner that the surface to be scanned is immersed in said body of liquid.

4. Apparatus according to claim 3 wherein said holding means is arranged to hold the casting or other body in such a manner that the surface to be scanned faces downwards and lies at or just below the surface of said body of liquid.

5. Apparatus according to claim 1 including means for mechanically urging said probe towards the surface of the casting or other body to be scanned.

6. Apparatus according to claim 5 wherein said probe comprises a probe member and a sleeve in which said probe member is mounted and which spaces said probe member a constant small distance away from the casting or other body.

7. Apparatus according to claim 6 wherein said probe includes spring-loaded links for urging said sleeve into contact with the surface to be scanned.

8. Apparatus according to claim 5 including monitoring means for monitoring the force with which said probe is urged towards the surface to be scanned.

9. Apparatus according to claim 8 wherein said monitoring means comprises at least one strain gauge.

10. Apparatus according to claim 8 wherein said display means include a signal lamp in view of the operator which is illuminated when the force monitored by said monitoring means is within a predetermined range.

11. Apparatus according to claim 1 wherein said gating means is arranged to gate signals from said signal generating-receiving means in conjunction with information on the instantaneous position of the probe so as to eliminate signals from known sources and pass on only anomalous signals arising from defects.

12. Apparatus according to claim 11 wherein said pointer incorporates a light for displaying the occurrence of anomalous signals.

13. Apparatus according to claim 11 wherein said display means includes means for producing audible signals to indicate the occurrence of anomalous signals.

* * * * *